United States Patent [19]

Kolich

[11] Patent Number: 4,633,026
[45] Date of Patent: Dec. 30, 1986

[54] PROCESS FOR PREPARING RING-HALOGENATED VINYL AROMATIC MONOMERS

[75] Inventor: Charles H. Kolich, Baton Rouge, La.

[73] Assignee: Ethyl Corporation, Richmond, Va.

[21] Appl. No.: 656,432

[22] Filed: Oct. 1, 1984

Related U.S. Application Data

[63] Continuation-in-part of Ser. No. 468,061, Feb. 22, 1983, abandoned.

[51] Int. Cl.$^4$ .............................................. C07C 17/34
[52] U.S. Cl. ..................................... 570/200; 570/193
[58] Field of Search ................ 570/200, 143, 193, 204

[56] References Cited

U.S. PATENT DOCUMENTS

| | | | |
|---|---|---|---|
| 4,292,453 | 9/1981 | Daren et al. | 570/193 |
| 4,338,474 | 7/1982 | Jackisch | 570/105 |
| 4,343,956 | 8/1982 | Jackisch | 570/105 |
| 4,376,221 | 3/1983 | Jackisch | 570/103 |

FOREIGN PATENT DOCUMENTS

573559 11/1945 United Kingdom ........... 260/654 D

OTHER PUBLICATIONS

Stott et al., Modified Crown Ether Catalysts. 3. Structural Parameters Affecting Phase Transfer Catalysis by Crown Ethers and a Comparison of the Effectiveness of Crown Ethers to That of Other Phase Transfer Catalysts, J. Am. Chem. Soc., vol. 102, No. 14, 1980, pp. 4810–4815.

Poly(ethylene glycols) are Extraordinary Catalysts in Liquid–Liquid Two Phase Dehydrohalogenation by Kimura et al.

*Primary Examiner*—Natalie Trousof
*Assistant Examiner*—Joseph A. Boska
*Attorney, Agent, or Firm*—Donald L. Johnson; John F. Sieberth; Edward F. Sherer

[57] ABSTRACT

A process for preparing ring-halogenated vinyl aromatic monomers comprising reacting ring-halogenated (alpha- or beta-bromoethyl)benzenes or ring-halogenated (alpha- or beta-bromoethyl)toluenes with a strong aqueous alkali base in the presence of a poly(ethylene glycol) catalyst and an amine selected from the group consisting of the structure:

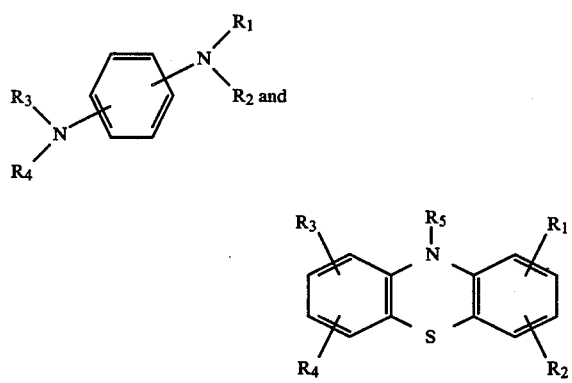

wherein $R_1$, $R_2$, $R_3$, $R_4$, and $R_5$ are independently selected from the group consisting of hydrogen and $C_1$ to $C_{10}$ alkyl groups. The organic phase is separated, washed and neutralized and the ring-halogenated vinyl aromatic monomer is recovered.

20 Claims, No Drawings

PROCESS FOR PREPARING RING-HALOGENATED VINYL AROMATIC MONOMERS

This application is a continuation-in-part of U.S. Ser. No. 468,061 filed Feb. 22, 1983, now abandoned.

BACKGROUND

1. Field of the Invention

The present invention relates to ring halogenated vinyl aromatic monomers used as flame retardants in vinyl aromatic based polymers, especially such styrene monomers and vinyl toluene monomers. More particularly, the present invention is directed to a process for preparing ring halogenated vinyl aromatic monomers from ring halogenated bromoethylbenzene or bromoethyltoluene using a strong aqueous alkali base, poly(ethylene glycol) catalyst and certain types of amine stabilizer.

2. Description of the Prior Art

The problem of the flammability of polymer compositions is well-recognized. A variety of compounds exist that provide satisfactory flame resistance, smoke suppression and self-extinguishing properties.

Vinyl aromatic polymers, especially styrene based polymers make up a significant part of the plastics industry. Polymers having styrene as part of their structural makeup are for example polystyrene, styrene-butadiene copolymers, ABS, SAN, thermosetting polyester resins and copolymers of styrene with acrylate and maleic monomers, and many others. Polymers having methyl styrene or vinyl toluene as part of their structural makeup are for example para-methylstyrene. A deficiency of these styrene or vinyl toluene based polymers however, is their flammability. Consequently, there is an ever increasing awareness and interest in providing polymers which possess flame retardance.

The article entitled "Elimination Reactions of Polyhalopropanes under Emulsion Catalytic Conditions to give Halopropenes" by Wang in *Synthesis* June, 1982, pages 494–496 mentions the use of sodium hydroxide for the dehydrohalogenation of haloalkanes. Certain phase transfer catalysts are also identified. In "Modified Crown Ether Catalysts. 3. Structural Parameters Affecting Phase Transfer Catalysis by Crown Ethers and a Comparison of the Effectiveness of Crown Ethers to That of Other Phase Transfer Catalysts" by Stott et al in *J. Am. Chem. Soc.*, Vol. 102, No. 14, 1980, pages 4810–4815, the effectiveness of poly(ethylene glycols) as phase-transfer catalysts is taught. In another article entitled "Poly(ethylene glycols) are Extraordinary Catalysts in Liquid-Liquid Two-Phase Dehydrohalogenation" by Kimura et al, *J. Org. Chem.* 47, 2493 (1982), the benefit of using poly(ethylene glycols) as catalyst in dehydrogenation reactions was recognized.

It was noted in U.S. Pat. No. 4,292,453 that when a reaction product containing about 5–10% dibromostyrene is stored for several hours before final workup some of the monomer polymerizes. The patent recommends the use of a nitrite salt as a monomer stabilizer during the reaction to reduce the amount of polymerization of bromostyrenes.

U.S. Pat. Nos. 4,338,474 and 4,343,956 recognize the use of a number of amines as stabilizers for dibromostyrene. These patents teach the addition of an amine directly to the dibromostyrene. The amines are not present during the synthesis of the dibromostyrene but merely function to prevent polymerization during storage.

It has now been discovered that by adding an aromatic amine polymerization inhibitor directly to the reaction during the preparation of ring-halogenated vinyl aromatic monomers along with a poly(ethylene glycol) catalyst and a strong aqueous alkali base that polymerization is inhibited and an increased yield of the ring-halogenated vinyl aromatic monomer is obtained.

SUMMARY OF THE INVENTION

In accordance with the present invention, ring-halogenated vinyl aromatic monomers are prepared by reacting ring-halogenated bromoethyl aromatic compounds with a strong aqueous alkali base along with a poly(ethylene glycol) catalyst and an aromatic amine.

The ring-halogenated bromoethyl aromatic compound has the following structure:

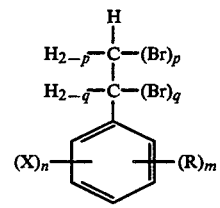

wherein p is 0 or 1, q is 0 or 1 and p+q=1; n is an integer from 1–5, m is 0, 1, or 2, and m+n=5; X is halogen; and, R is a $C_{1-12}$ alkyl group.

The aromatic amine is selected from the group consisting of

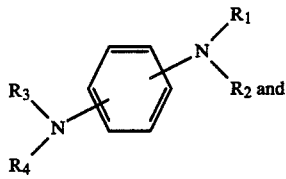

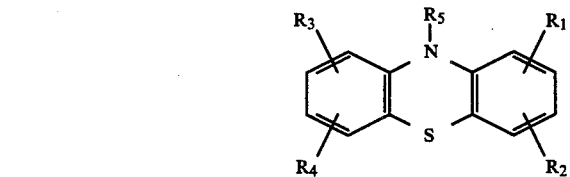

wherein $R_1$, $R_2$, $R_3$, $R_4$ and $R_5$ are independently selected from the group consisting of hydrogen and $C_1$ to $C_{10}$ alkyl.

The different phases are separated and the organic phase is washed and dried to isolate the ring-halogenated vinyl aromatic monomer.

DESCRIPTION OF THE PREFERRED EMBODIMENTS

The present invention is a process for preparing ring-halogenated vinyl aromatic monomers comprising (a) reacting a ring-halogenated bromoethyl aromatic compound with a strong aqueous alkali base in the presence of a poly(ethylene glycol) catalyst and an amine selected from the group consisting of the structure:

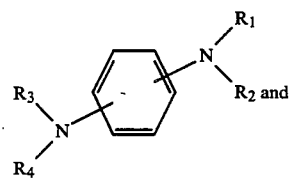

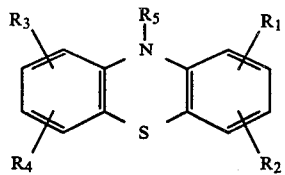

wherein R₁, R₂, R₃, R₄ and R₅ are independently selected from the group consisting of hydrogen and C₁ to C₁₀ alkyl; (b) separating the aqueous and organic phases; (c) washing and neutralizing said organic phase; and (d) recovering said ring-halogenated vinyl aromatic monomer from said organic phase.

The ring-halogenated bromoethyl aromatic compound of the present invention has the following structure:

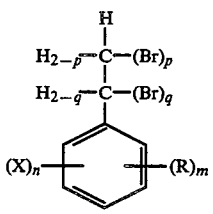

wherein p is 0 or 1, q is 0 or 1 and p+q=1; n is an integer from 1-5, m is 0, 1, or 2, and m+n=5; X is halogen; and R is a $C_{1-12}$ alkyl group.

The halogen may be bromine, chlorine, fluorine or iodine with chlorine or bromine being preferred and bromine being the most preferred.

Of the ring halogenated aromatic compounds, (bromoethyl)benzene and (bromoethyl)toluene derivatives are preferred, with the most preferred being (beta-bromoethyl)benzene and (beta-bromoethyl)toluene derivatives. Ring-halogenated bromoethyl aromatic compounds include (bromoethyl)benzenes, (bromoethyl)toluenes, (bromoethyl)ethylbenzenes, (bromoethyl)propylbenzenes, (bromoethyl)butylbenzenes, (bromoethyl)pentylbenzenes, (bromoethyl)hexylbenzenes, (bromoethyl)heptylbenzenes, (bromoethyl)octylbenzenes, (bromoethyl)nonylbenzenes, (bromoethyl)decylbenzenes, (bromoethyl)undecylbenzenes, and (bromoethyl)dodecylbenzenes. The bromoethyl group may be an alpha-bromoethyl group or a beta-bromoethyl group.

Typical (alpha-bromoethyl)benzenes include (alpha-bromoethyl)-o-fluorobenzene, (alpha-bromoethyl)-p-iodobenzene, (alphabromoethyl)-o-chlorobenzene, (alpha-bromoethyl)-m-chlorobenzene, (alpha-bromoethyl)-p-chlorobenzene, (alpha-bromoethyl)-2,4-dichlorobenzene, (alpha-bromoethyl)-3,4-dichlorobenzene, (alpha-bromoethyl)-2,3,6-trichlorobenzene, (alpha-bromoethyl)-3,4,5-trichlorobenzene, (alpha-bromoethyl)-p-bromobenzene, (alpha-bromoethyl)-o-bromobenzene, (alpha-bromoethyl)-m-bromobenzene, (alpha-bromoethyl)-2,4-dibromobenzene, (alpha-bromoethyl)-3,4-dibromobenzene, (alpha-bromoethyl)-2,5-dibromobenzene, (alpha-bromoethyl)-2,6-dibromobenzene, (alpha-bromoethyl)-2,4,5-tribromobenzene, (alpha-bromoethyl)-2,4,6-tribromobenzene and (alphabromoethyl)-2,3,4-tribromobenzene.

Typical (beta-bromoethyl)benzenes include (beta-bromoethyl)-o-fluorobenzene, (beta-bromoethyl)-p-iodobenzene, (beta-bromoethyl)-o, m- or p-chlorobenzene, (beta-bromoethyl)-2,4-dichlorobenzene, (beta-bromoethyl)-3,4-dichlorobenzene, (beta-bromoethyl)-2,3,6-trichlorobenzene, (beta-bromoethyl)-3,4,5-trichlorobenzene, (beta-bromoethyl)-m-bromobenzene, (beta-bromoethyl)-o-bromobenzene, (beta-bromoethyl)-m-bromobenzene, (beta-bromoethyl)-2,4-dibromobenzene, (beta-bromoethyl)-3,4-dibromobenzene, (beta-bromoethyl)-2,5-dibromobenzene, (beta-bromoethyl)-2,6-dibromobenzene, (beta-bromoethyl)-2,4,5-tribromobenzene, (beta-bromoethyl)-2,4,6-tribromobenzene, (beta-bromoethyl)-2,3,4-tribromobenzene, (beta-bromoethyl)-2-bromo-4-chlorobenzene, (beta-bromoethyl)pentachlorobenzene, etc. and mixtures of any of these.

Typical (alpha-bromoethyl)toluenes include 4-(alpha-bromoethyl)-2-bromotoluene, 2-(alpha-bromoethyl)-3-chlorotoluene, 3-(alpha-bromoethyl)-2-iodotoluene, 4-(alpha-bromoethyl)-2-fluorotoluene, 4-(alpha-bromoethyl)-2,6-dibromotoluene, 4-(alpha-bromoethyl)-3,5-dichlorotoluene, 4-(alpha-bromoethyl)-2,3,6-tribromotoluene, 4-(alpha-bromoethyl)-2,3,5-trichlorotoluene, and 4-(alpha-bromoethyl)-2,3,5,6-tetrabromotoluene.

Typical (beta-bromoethyl)toluenes include 4-(beta-bromoethyl)-2-chlorotoluene, 2-(beta-bromoethyl)-3-bromotoluene, 3-(beta-bromoethyl)-2-fluorotoluene, 4-(beta-bromoethyl)-2-iodotoluene, 4-(beta-bromoethyl)-2,6-dichlorotoluene, 4-(beta-bromoethyl)-b 3,5-dibromotoluene, 4-(beta-bromoethyl)-2,3,6-trichlorotoluene, 4-(beta-bromoethyl)-2,3,5-tribromotoluene, and 4-(beta-bromoethyl)-2,3,5,6-tetrachlorotoluene.

Other typical ring-halogenated bromoethyl compounds are 1-(beta-bromoethyl)-2-bromo-4-ethylbenzene, 1-(alpha-bromoethyl)-2-chloro-3-propylbenzene, 1-(beta-bromoethyl)-3-bromo-4-butylbenzene, 1-(alpha-bromoethyl)-3-chloro-4-pentylbenzene, 1-(beta-bromoethyl)-2-fluoro-4-hexylbenzene, 1-(alpha-bromoethyl)-3-iodo-4-heptylbenzene, 1-(beta-bromoethyl)-2,6-dichloro-4-octylbenzene, 1-(alpha-bromoethyl)-3,5-dibromo-4-nonylbenzene, 1-(beta-bromoethyl)-2,3,6-tribromo-4-decylbenzene, 1-(alpha-bromoethyl)-2,3,5-trichloro-4-undecylbenzene, 1-(beta-bromoethyl)-2,3,5,6-tetrabromo-4-dodecylbenzene.

It can be appreciated that the foregoing are only representative of the numerous ring-halogenated aromatic compounds which can be used in the process of this invention.

Preferred starting materials are (beta-bromoethyl)monobromobenzene, (beta-bromoethyl)dibromobenzene, (beta-bromoethyl)tribromobenzene or mixture of these benzenes, and (beta-bromoethyl)-ar-monobromotoluene, (beta-bromoethyl)-ar-dibromotoluene, (beta-bromoethyl)-ar-tribromotoluene or mixture of these toluenes. Even more preferred starting materials are (beta-bromoethyl)-3,4-dibromobenzene, (beta-bromoethyl)-2,4-dibromobenzene, (beta-bromoethyl)-2,5-dibromobenzene, (beta-bromoethyl)-2,6,-dibromobenzene, 4-(beta-bromoethyl)-2,3-dibromotoluene, 4-(beta-bromoethyl)-2,5-dibromotoluene, 4-(beta-bromoethyl)-2,6-dibromotoluene, and 4-(beta-bromoethyl)-3,5-dibromotoluene.

The strong aqueous alkali base solutions contemplated for reacting with the ring-halogenated bromoethyl aromatic compounds are usually solutions of sodium hydroxide or potassium hydroxide in concentrations of about from 20 to 75% and preferably 20 to 60%. The mole ratio of alkali base solutions to ring-halogenated bromoethyl aromatic compound may be from 1.5:1 to 10:1, usually 2:1 to 6:1 and preferably 2:1 to 4:1. Other ratios may be used, but, for practical reasons, it is desirable to use the least amount of base possible. It has been found that about 4 equivalents of 50 weight percent aqueous sodium hydroxide give complete elimination of HBr in about 3 hours at 25°-30° C. However, 2 equivalents of 50%, NaOH can produce the same result if the reaction temperature is increased to about 45° C. Upon completion of the reaction, the precipitated NaBr can be readily filtered off and recycled to recover the bromine value. The residual dilute aqueous alkali base filtrate can be recycled to the reaction after an appropriate amount of the solid alkali metal hydroxide is added to restore the original concentration. The strong alkali base solutions may be added all at one time, in stages, or there can be an initial charge of about one equivalent of 50 weight percent aqueous alkali metal hydroxide followed by the gradual addition of solid alkali metal hydroxide to prevent the base concentration from falling below the preferred minimum level of 30–40 weight percent. Alternatively, a reverse addition can be employed; that is, the ring-halogenated (bromoethyl)aromatic compound can be added to the aqueous alkali metal hydroxide solution. In this case, it is most convenient to dissolve the amine polymerization inhibitor in the organic feed and charge the glycol catalyst with the aqueous base.

Poly(ethylene glycols) having the formula: $HO(CH_2CH_2O)_nH$ where n is greater than 3 are highly active and selective in catalyzing dehydrohalogenation in organic-aqueous hydroxide two-phase systems. It is speculated that the effectiveness of poly(ethylene glycols) as dehydrohalogenation catalysts is likely due to the relationship of the terminal hydroxy group and the ether linkages. Poly(ethylene glycols) having average molecular weights of 200 to 3400 are preferred. The amount of the poly(ethylene glycol) catalyst may be anywhere from 0.01 weight percent to 20 weight percent of the ring-halogenated (bromoethyl) aromatic compound and preferably between about 0.1 to 1.0 weight percent.

The preferred amines used in the practice of the present invention include:

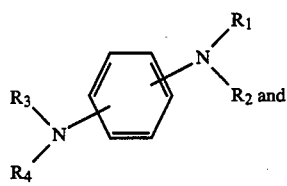

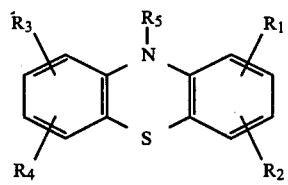

wherein $R_1$, $R_2$, $R_3$, $R_4$ and $R_5$ are independently selected from the group consisting of hydrogen and $C_1$ to $C_{10}$ alkyl. Examples of compounds within structure I include:

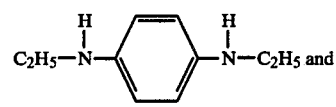

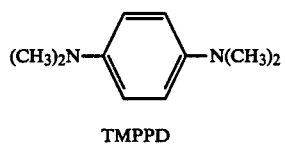

TMPPD

Examples of compounds within structure II include:

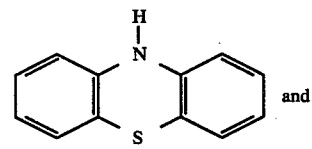

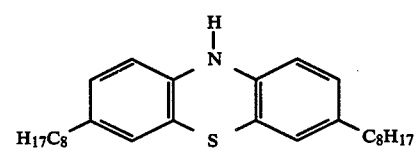

These amines are intended to inhibit polymerization of the product during the course of the reaction. The preferred polymerization inhibitor in the practice of the present invention is N,N,N',N'-tetramethyl-p-phenylene diamine (TMPPD). The amount of amine is generally within the range of 10 parts per million to about 10,000 parts per million based on the amount of the ring halogenated bromoethyl aromatic compound. Preferably, the amine is in the range of about 400 to 600 parts per million.

In the presence of even a small amount of poly(ethylene glycol), the reaction in the case of ring-halogenated bromoethyl aromatic compounds proceeds to completion in a very short time. The time is dependent on the temperature of the reaction which can range from about 0° C. to about 120° C. depending on the type and number of halogens substituted on the ring. In the case of (beta-bromoethyl)dibromobenzene, the preferred temperature is within the range of about 10° C. to about 70° C., and more preferably from about 15° C. to about 30° C. Mild reaction conditions are preferred.

EXAMPLE 1

Brominated Styrene Preparation Under Nitrogen With No Polymerization Inhibitor Present A 213.9 g (0.624 mole) portion of a mixture of ring brominated (beta-bromoethyl)benzenes consisting of 7.5% (beta-bromoethyl)monobromobenzenes, 85.9% (beta-bromoethyl)dibromobenzenes, and 5.8% (beta-bromoethyl)tribromobenzenes (Gas Chromatograph area percent) was combined with 1.02 g of poly(ethylene gylcol), average molecular weight of 600, in a 500-ml flask. A nitrogen atmosphere was maintained in the flask during the reaction. A 49.2 g (0.615 mole) portion of 50 weight percent aqueous NaOH was added to the reaction mixture in 15 min at 26°–35° C. After stirring for 10 minutes at 35° C., intermittent ice bath cooling was used to maintain the temperature at 32°–38° C. while 24.9 g (0.623 mole) of solid NaOH was added in 2–5 g portions in 30 minutes. A 6.2 g sample (sample A) of the organic phase was removed 1 hour after the completion of the NaOH addition. Sample A was washed with 3 M HCl and dried with MgSO$_4$. Dilution of 2.14 g of sample A with 40 ml methanol gave 0.05 g of insoluble polymer (2.3 weight percent). After stirring the reaction mixture for a total of 3.5 hours at 35°–45° C., the mixture was cooled to 25° C., and 75.8 g of water was added. The yellow organic phase was separated and washed with 63.1 g of 0.6 M HCl. The recovered cloudy yellow organic phase was then dried under vacuum to obtain 154.8 g (98.3% yield) of clear yellow product (Sample B). Dilution of 10.04 g of the product with 200 ml methanol gave 0.29 g of insoluble polymer (2.9 weight percent). Gas chromatographic analysis for the samples are given in Table 1.

TABLE 1

| Component | GC Analysis (area %) Sample A | Sample B |
|---|---|---|
| monobromostyrene | 2.8 | 7.2 |
| dibromostyrene | 84.1 | 90.0 |
| tribromostyrene | 3.5 | 2.7 |
| (beta-bromoethyl)monobromobenzene | 5.0 | 0.0 |
| (beta-bromoethyl)dibromobenzene | 4.5 | 0.2 |
| (beta-bromoethyl)tribromobenzene | 0.2 | 0.0 |

EXAMPLE 2

Preparation with Air Sparge and No Polymerization Inhibitor Present

Example 2 was carried out as described in Example 1, except the reaction mixture was sparged with air at a flow rate of 1.3 liter/min throughout the NaOH addition and subsequent 3 hour cook at 30°–40° C. The yield of clear light yellow product was 96.5%. Polymer content by 40:1 (v/v%) dilution with methanol was 0.8 weight percent. GC analysis of the product indicated a composition of 88.6% dibromostyrene, 6.6% monobromostyrene, 4.7% tribromostyrene, and 0.1% (beta-bromoethyl)dibromobenzene.

EXAMPLE 3

Preparation with N,N,N',N'-Tetramethyl-p-Phenylene Diamine Inhibitor

Example 3 was similar to Example 1 except that the reaction mixture was open to the atmosphere (but not sparged with air) and 1000 ppm [based on (beta-bromoethyl)bromobenzene mixture] of N,N,N',N'-tetramethyl-p-phenylene diamine was added to the aromatic compound before starting the NaOH addition. The yield of light yellow product was 98.1% and composition by gas chromatography (area %) was 88.8% dibromostyrene, 6.9% monobromostyrene, 3.9% tribromostyrene, and 0.3% (beta-bromoethyl)dibromobenzene. Dilution of 10.19 g of the product with 200 ml methanol gave only 0.01 g of insoluble polymer (0.1 weight percent).

The results of Examples 1 to 3 are listed in Table 2.

TABLE 2

| Example | Air Sparge (l/min) | Amount TMPPD (ppm) | Polymer Formed (wt %) | Brominated Styrene Yield (%) |
|---|---|---|---|---|
| 1 | 0 (N$_2$ atoms) | 0 | 2.9 | 98.3 |
| 2 | 1.3 | 0 | 0.8 | 96.5 |
| 3 | 0 (air atoms) | 1000 | 0.1 | 98.1 |

EXAMPLE 4

Scale-Up of Brominated Styrene Preparation

A 10-gal glass-lined reactor was charged with 56 lb (0.700 lb mole) of 50 weight percent aqueous NaOH and 136 g of poly(ethylene glycol) catalyst (ave. mole wt. of 600). A 59.4 lb (0.173 lb-mole) portion of ring brominated (beta-bromoethyl)benzenes containing 14 g (500 ppm) of N,N,N',N'-tetramethyl-p-phenylene diamine polymerization inhibitor was fed into the reactor in 2 hours at a temperature of 18°–28° C. The composition of the (beta-bromoethyl)bromobenzene mixture by gas chromatography was 4.3 area percent (beta-bromoethyl)monobromobenzenes, 86.9 area percent (beta-bromoethyl)dibromobenzenes, 5.8 area percent (beta-bromoethyl)tribromobenzenes, 2.7 area percent ar-dibromostyrenes, and 0.3 area percent ar-tribromostyrene. Air was passed into the reaction mixture throughout the run at a rate of about 10 std. cubic feet per hour. After adding the ring brominated (beta-bromoethyl)-benzenes, the mixture was stirred at 27°–31° C. for 3.5 hours to complete the reaction. About 10 lb of water was added to dissolve precipitated salts, and the lower organic phase was removed. After washing with 16.7 lb of 0.6 M HCl, the organic phase was dried under vacuum to give 41.8 lb (92% yield) of clear yellow product. GC analysis (area %) indicated a composition of 91.2% dibromostyrene, 7.4% monobromostyrene, and 1.4% tribromostyrene. Polymer content as determined by 40:1 (v/v%) dilution with methanol was 0.1 weight percent.

EXAMPLE 5

Preparation of ar-Dibromo-p-methylstyrene

A 500-ml reaction flask was charged with 50% sodium hydroxide (175 g, 2.19 mole) and poly(ethylene glycol) (0.92 g). A solution of N,N,N',N',-tetramethyl-p-phenylenediamine (0.098 g) (beta-bromoethyl)dibromotoluene (184.5 g, 0.517 mole) and methylene chloride (10 ml) was added from an addition funnel to the caustic mixture over 0.5 hour at 18°–30° C. (cooling required). The addition funnel was rinsed with methylene chloride, to give a total of 20 ml solvent in the reaction mixture. The tan mixture was stirred for 0.1 hour with cooling, and the bath was removed. The exotherm continued for 0.2 hours and reached a maximum of 30° C. A heating mantle was then required to maintain the temperature at 27°–30° C. for an additional 2.3 hours. The mixture was cooled to 18° C. and water (50 g) was added with virorous stirring. The temperature rose to 26° C. and solid deposition began. Chloroform (100 ml) was added, giving a brown solution. After transferring to a separatory funnel, with chloroform and water rinse, the mixture was shaken gently. After standing 0.2 hours, the organic phase was drawn off. The aqueous layer was re-extracted with chloroform (50 ml) and the combined extracts were washed with 0.6 M HCl. The very hazy organic layer was transferred to a tared, 500 ml boiling flask containing 4-tert-butylcatechol (0.0328 g). After vacuum stripping to remove solvent and water, a residual oil was obtained (142.6 g, 99.9% yield) which gave the following analysis by capillary gas chromatograph:

| Compound | Area % |
|---|---|
| ar-mononbromo-p-methylstyrenes | 0.2 |
| ar-dibromo-m&p-methylstyrenes | 98.6 |
| ar-tribromo-p-methylstyrenes | 0.3 |
| "other" | 0.9 |

A 40:1 (v/v %) methanol dilution indicated the product contained 0.4% polymer. The product was re-processed by warming to about 40° C., charging to an addition funnel and slowly (1 hour) adding to vigorously stirred methanol (2 liters). The methanol solution was then filtered and the filtrate vacuum-stripped to give ar-dibromo-p-methylstyrene (134 g). A methanol test on the re-worked product gave 0.1% polymer.

EXAMPLE 6

Preparation of ar-Dibromo-p-methylstyrene

An addition funnel was charged with a mixture of distilled (beta-bromoethyl)-ar-dibromotoluene (BEDBT) (304.6 g, 0.853 mole) and N,N,N',N',-tetramethyl-p-phenylenediamine (0.16 g). A 1-liter reaction flask was charged with 50% NaOH (292 g, 3.65 moles) and poly(ethylene glycol), average molecular weight of 600 (1.54 g). The caustic was stirred vigorously as the BEDBT was added at 22°–29° C. over 53 min. with ice bath cooling. The ice-bath was removed 12 minutes after completion of the BEDBT addition. In the next 20 min., the temperature rose from 26° to 31° C. After an additional 70 min. cook time the temperature slowly decreased to 27° C. Application of external heat kept the temperature at 27°–28° C. for the balance of the 3.0 hour cook period.

The reaction mass was cooled to 22° C., with resultant thickening and solid deposition. Water (100 ml) and chloroform (100 ml) were added. The mixture was stirred vigorously for a few min. and transferred to a separatory funnel with water and chloroform rinse. After standing for 5 min., the brown organic layer was drawn off and washed with 0.6 M HCl (300 ml). The hazy yellow organic layer was drawn off into a round-bottom flask containing 0.05 g 4-tert-butylcatechol. The hazy product was vacuum dried at 1–2 torr/25° C. on a rotary evaporator to give 234 g (99.4% yield) dibromo-p-methylstyrene (DBPMS). A methanol insolubles test indicated 0.1% polymer content. A gas chromatographic analysis of the DBPMS gave the following result:

| Compound | Area % |
|---|---|
| ar-monobromo-p-methylstyrene | 0.4 |
| ar-dibromo-p-methylstyrene | 98.5 |

-continued

| Compound | Area % |
|---|---|
| ar-tribromo-p-methylstyrene | 0.3 |
| (beta-bromoethyl)dibromotoluene | 0.5 |
| (beta-bromoethyl)tribromotoluene | 0.1 |
| Other | 0.3 |

A stability comparison was made between the DBPMS stabilized with 230 ppm 4-tert-butylcatechol and dibromostyrene which had about 215 ppm 4-tert-butylcatechol. After 312 hours at 50° C. (shaker-bath), the DBS contained 3.8% polymer by the methanol dilution test while the DBPMS contained 2.0% polymer. Both products, prior to test, contained 0.1% polymer.

Although the process of this invention is particularly suitable for making compounds such as dibromostyrene and dibromo-p-methylstyrene, and other similar type compounds, no claim is made to such compounds as they are the invention of others.

The foregoing disclosure and description of the invention is illustrative and explanatory thereof and various changes in the illustrated process may be made within the scope of the appended claims without departing from the spirit of the invention.

I claim:

1. A process for preparing ring-halogenated vinyl aromatic monomers comprising:

(a) reacting in the presence of air a ring-halogenated bromoethyl aromatic compound having the following structure:

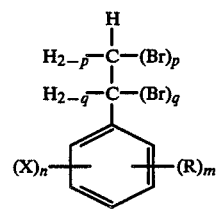

wherein p is 0 or 1, q is 0 or 1, and p+q=1; n is an integer from 1–5, m is 0, 1 or 2, and m+n=5; is halogen; and, R is a $C_{1-12}$ alkyl group, with a strong aqueous alkali base in the presence of a poly(ethylene glycol) catalyst and an amine polymerization inhibitor selected from the group consisting of the structure:

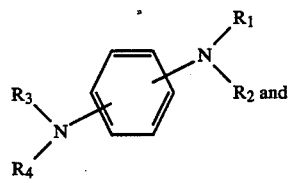

and

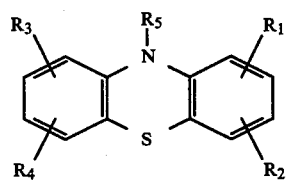

wherein $R_1$, $R_2$, $R_3$, $R_4$ and $R_5$ are independently selected from the group consisting of hydrogen and $C_1$ to $C_{10}$ alkyl;

(b) separating the aqueous and organic phases; and (c) recovering said ring-halogenated vinyl aromatic monomer from said organic phase.

2. A process according to claim 1, wherein the reaction is carried out at a temperature from 0° C. to 120° C.

3. A process according to claim 1, wherein said ring-halogenated (bromoethyl)aromatic compound is selected from the group consisting of (alpha- or beta-bromoethyl)monobromobenzenes; (alpha or beta-bromoethyl)dibromobenzenes; (alpha- or beta-bromoethyl)tribromobenzenes and mixtures thereof and (alpha- or beta-bromoethyl)-monochloro-, dichloro-, and trichlorobenzenes and mixtures thereof.

4. A process according to claim 1, wherein said ring-halogenated (bromoethyl)aromatic compound is (alpha-bromoethyl)dibromobenzene.

5. A process according to claim 1, wherein said ring-halogenated (bromoethyl)aromatic compound is (beta-bromoethyl)dibromobenzene.

6. A process according to claim 1, wherein said ring-halogenated (bromoethyl)aromatic compound is selected from the group consisting of (alpha- or beta-bromoethyl)-ar-monobromotoluenes; (alpha- or beta-bromoethyl)-ar-dibromotoluenes; (alpha- or beta-bromoethyl)-ar-tribromotoluene and mixtures thereof and (alpha- or beta-bromoethyl)-monochloro-, dichloro-, and trichlorotoluenes and mixtures thereof.

7. A process according to claim 1, wherein said ring-halogenated (bromoethyl)aromatic compound is (alpha-bromoethyl)-ar-dibromotoluene.

8. A process according to claim 1, wherein said ring-halogenated (bromoethyl)aromatic compound is (beta-bromoethyl)-ar-dibromotoluene.

9. A process according to claim 1, wherein said amine is N,N,N',N'-tetramethyl-p-phenylene diamine.

10. A process according to claim 1, wherein said poly(ethylene glycol) catalyst has a molecular weight from about 200 to about 3400.

11. A process according to claim 1, wherein the mole ratio of said strong aqueous alkali base to the ring-halogenated (bromoethyl)aromatic compound is from 1.5:1 to 10:1.

12. A process according to claim 1, wherein the concentration of said strong aqueous alkali base is 20% to 75% by weight and said strong aqueous alkali base is selected from the group consisting of sodium hydroxide and potassium hydroxide.

13. A process according to claim 1, wherein the reaction is conducted in a plurality of stages, wherein spent aqueous alkali base is withdrawn and fresh aqueous alkali base is added.

14. A process according to claim 1, wherein solid alkali metal hydroxide is added during the course of the reaction.

15. A process according to claim 1, wherein said (bromoethyl)aromatic compound is added to the strong aqueous alkali base.

16. A process according to claim 1, wherein said ring-halogenated bromoethyl aromatic compound has an alkyl group of from 1 to 12 carbon atoms attached directly to the benzene ring.

17. A process according to claim 16, wherein said alkyl group is attached to the benzene ring in the para position.

18. A process according to claim 1, wherein said ring-halogenated bromoethyl aromatic compound is (beta-bromoethyl)-ar-tribromotoluene.

19. A process according to claim 1, wherein said ring-halogenated bromoethyl aromatic compound is (beta-bromoethyl)-ar-trichlorotoluene.

20. A process according to claim 1, wherein said ring-halogenated bromoethyl aromatic compound is (alpha-bromoethyl)-ar-tribromotoluene.

* * * * *

UNITED STATES PATENT AND TRADEMARK OFFICE
CERTIFICATE OF CORRECTION

PATENT NO. : 4,633,026
DATED : DECEMBER 30, 1986
INVENTOR(S) : CHARLES H. KOLICH

It is certified that error appears in the above-identified patent and that said Letters Patent is hereby corrected as shown below:

Column 4, Line 35, reads "4-(beta-bromoethyl)-b 3,5" and should read -- 4-(beta-bromoethyl)-3,5 --.

Column 10, Line 46, reads "m + n = 5; is" and should read -- m + n = 5; X is --.

Signed and Sealed this

Eighteenth Day of August, 1987

Attest:

DONALD J. QUIGG

Attesting Officer

Commissioner of Patents and Trademarks